US009771291B2

(12) United States Patent
Knauf et al.

(10) Patent No.: US 9,771,291 B2
(45) Date of Patent: Sep. 26, 2017

(54) PROCESS FOR WORKING UP WASTE WATER FROM NITROBENZENE PREPARATION

(71) Applicant: COVESTRO DEUTSCHLAND AG, Leverkusen (DE)

(72) Inventors: Thomas Knauf, Dormagen (DE); Antoni Mairata, Dusseldorf (DE); Erik Sluyts, Brasschaat (BE); Jan Van Tricht, Ekeren (BE)

(73) Assignee: Covestro Deutschland AG, Leverkusen (DE)

( * ) Notice: Subject to any disclaimer, the term of this patent is extended or adjusted under 35 U.S.C. 154(b) by 192 days.

(21) Appl. No.: 14/784,699

(22) PCT Filed: Apr. 14, 2014

(86) PCT No.: PCT/EP2014/057488
§ 371 (c)(1),
(2) Date: Oct. 15, 2015

(87) PCT Pub. No.: WO2014/170250
PCT Pub. Date: Oct. 23, 2014

(65) Prior Publication Data
US 2016/0060152 A1    Mar. 3, 2016

(30) Foreign Application Priority Data
Apr. 18, 2013 (EP) .................................... 13164307

(51) Int. Cl.
| C02F 9/00 | (2006.01) |
| C02F 1/02 | (2006.01) |
| C02F 1/20 | (2006.01) |
| C07C 201/08 | (2006.01) |
| C07C 201/16 | (2006.01) |
| C07C 209/36 | (2006.01) |
| C02F 1/04 | (2006.01) |
| C02F 101/32 | (2006.01) |
| C02F 101/38 | (2006.01) |
| C02F 103/18 | (2006.01) |

(52) U.S. Cl.
CPC ................ *C02F 9/00* (2013.01); *C02F 1/025* (2013.01); *C02F 1/20* (2013.01); *C07C 201/08* (2013.01); *C07C 201/16* (2013.01); *C07C 209/36* (2013.01); *C02F 1/04* (2013.01); *C02F 2101/322* (2013.01); *C02F 2101/38* (2013.01); *C02F 2103/18* (2013.01); *C02F 2209/06* (2013.01); *C02F 2301/046* (2013.01)

(58) Field of Classification Search
None
See application file for complete search history.

(56) References Cited

U.S. PATENT DOCUMENTS

| 2,256,999 | A | 9/1941 | Castner |
| 2,739,174 | A | 3/1956 | Ross |
| 3,780,116 | A | 12/1973 | Sahgal |
| 4,230,567 | A | 10/1980 | Larbig |
| 4,772,757 | A | 9/1988 | Lailach et al. |
| 5,232,605 | A | 8/1993 | Baur et al. |
| 5,334,781 | A | 8/1994 | Kouwenhoven et al. |
| 5,763,697 | A | 6/1998 | Gebauer et al. |
| 6,288,289 | B1 | 9/2001 | Boyd et al. |
| 6,562,247 | B2 | 5/2003 | Gillis et al. |
| 7,326,816 | B2 | 2/2008 | Knauf et al. |
| 7,344,650 | B2 | 3/2008 | Knauf et al. |
| 7,763,759 | B2 | 7/2010 | Knauf et al. |
| 7,781,624 | B2 | 8/2010 | Rausch et al. |
| 2012/0078015 | A1 | 3/2012 | Zeeuw et al. |
| 2012/0228218 | A1 | 9/2012 | Fritz et al. |

FOREIGN PATENT DOCUMENTS

| EP | 0078247 | 11/1985 |
| EP | 0436443 | 7/1991 |
| EP | 0953546 | 11/1999 |
| WO | 2008148608 | 12/2008 |
| WO | 2011021057 | 2/2011 |
| WO | 2012025393 | 3/2012 |

OTHER PUBLICATIONS

Nitrobenzene fact sheet: support document, OPPT Chemical Fact Sheets, Feb. 1, 1995, XP055081053, www.epa.gov/chemfact/nitro-sd.pdf.

*Primary Examiner* — Duane Smith
*Assistant Examiner* — Phillip Shao
(74) *Attorney, Agent, or Firm* — N. Denise Brown; Donald R. Palladino

(57) ABSTRACT

The invention relates to a process for working up alkaline waste water which is formed during washing of crude nitrobenzene obtained by nitration of benzene, wherein
(i) the alkaline waste water is heated under an increased pressure with respect to atmospheric pressure with exclusion of oxygen and is then cooled and expanded;
(ii) the waste water obtained in (i) is purified further by stripping with a stripping gas and the stripping gas stream loaded with impurities is then cooled to a temperature of from 10° C. to 60° C.; and
(iii) the liquid process product obtained in (ii) by cooling the stripping gas stream loaded with impurities is separated into an aqueous and an organic phase and the organic phase is used further in an aniline production process.

9 Claims, No Drawings

PROCESS FOR WORKING UP WASTE WATER FROM NITROBENZENE PREPARATION

CROSS-REFERENCE TO RELATED APPLICATIONS

This Application is a National Phase Application of PCT/EP2014/057488, filed Apr. 14, 2014, which claims priority to European Application No. 13164307.4, filed Apr. 18, 2013, each of which being incorporated herein by reference.

FIELD

The invention relates to a process fix working up alkaline waste water which is formed during washing of crude nitrobenzene obtained by nitration of benzene, wherein
(i) the alkaline waste water is heated under an increased pressure with respect to atmospheric pressure with exclusion of oxygen and is then cooled and expanded;
(ii) the waste water obtained in (i) is purified further by stripping with a stripping gas and the stripping gas stream loaded with impurities is then cooled to a temperature of from 10° C. to 60° C.;
(iii) the liquid process product obtained in (ii) by cooling the stripping gas stream loaded with impurities is separated into an aqueous and an organic phase and the organic phase is used further in an aniline production process.

BACKGROUND

Nitrobenzene is an important intermediate product of the chemical industry which is required in particular for the preparation of aniline and therefore also for the preparation of di- and polyisocyanates of the diphenylmethane series and the polyurethanes based thereon.

The nitration of benzene with nitric acid to give a crude nitrobenzene has already been the subject of numerous publications and patent applications. The present current processes substantially correspond to the concept of adiabatic nitration of benzene by a mixture of sulfuric and nitric acid (so-called mixed acid). Such a process was claimed for the first time in U.S. Pat. No. 2,256,999 and is described in present-day embodiments, for example, in EP 0 436 443 B1, EP 0 771 783 B1 and U.S. Pat. No. 6,562,247 B2. The processes with an adiabatic reaction procedure are distinguished in particular in that no technical measures are taken to supply heat to or remove heat from the reaction mixture.

Isothermal processes for the nitration of benzene with mixed acid are also described, such as are described, for example, in EP 0 156 199 B1.

Processes for the nitration of benzene which manage without the use of sulfuric acid are also known. These are described, for example, in U.S. Pat. No. 2,739,174 or U.S. Pat. No. 3,780,116.

Gas phase processes for the nitration of benzene with nitric acid or nitrogen oxides are in principle also possible, but the yields which can thereby be achieved are still low (EP 0 078 247 B1, EP 0 552 130 B1).

All these processes have the common feature that the reaction product first formed is a crude nitrobenzene which comprises nitric acid and—if the nitration has been carried out with mixed acid—sulfuric acid, as well as dinitrobenzene and nitrated oxidation products of the benzene, in particular nitrated phenols (nitrophenols), as organic impurities. It also comprises organic compounds which are formed from the compounds which the benzene employed contains as impurities (WO 2008/148608 A1). The crude nitrobenzene moreover also comprises metal salts, which can be present in dissolved form in the acid residues or in the crude nitrobenzene (DE 10 2007 059 513 A1).

Numerous investigations in the past have been targeted at improving the quality of the crude nitrobenzene and thus at increasing the yield with respect to benzene and nitric acid. Thanks to these developments, the present-day adiabatic liquid phase processes have developed to the extent that they all succeed in preparing a crude nitrobenzene which has a low content of by-products, that is to say in general comprises only between 100 ppm and 300 ppm of dinitrobenzene and between 1,500 ppm and 2,500 ppm of nitrophenols it being possible for picric acid to assume a content of from 10% to 50% of the nitrophenols.

The crude nitrobenzene still contains as impurities water, benzene and nitrophenols and dinitrobenzene and—if the nitration has been carried out with mixed acid—sulfuric acid. These impurities are undesirable, since in subsequent processes where nitrobenzene is employed, such as, the example, the preparation of aniline, they can adversely influence these. Suitable work-up processes which comprise washing and distillation steps are described e.g. in U.S. Pat. No. 6,288,289 B1, EP 1 593 654 A1, EP 1 816 117 B1 and WO 2011/021057 A1.

EP 1 816 117 B1 describes the work-up of the crude nitrobenzene in an acid wash, an alkaline wash with aqueous sodium hydroxide solution, a neutral wash and a final purification by distillation. In principle bases other than sodium hydroxide solution can or course also be used, such as, for example, aqueous sodium carbonate solution or aqueous ammonia solution (WO 2011/082 977 A1) or potassium hydroxide or ammonia (DE 60 113 579 T2).

The work-up of the alkaline waste water from the alkaline wash can be carried out e.g. by thermal pressure decomposition (TPD). The fundamental process of TPD for treatment of waste waters comprising aromatic nitro compounds is described in the following patents:

EP 0 005 203 B1 describes a process for working up waste waters comprising nitro-hydroxyaromatics, wherein the waste waters are treated under a pressure of from 50 bar to 250 bar at a temperature of from 150° C. to 500° C. with exclusion of air and oxygen.

EP 0 503 387 B1 has described a similar process, which, however, is characterized in that the said alkaline waste water is worked up by addition of nitric acid and subsequent treatment in temperature ranges of from 180° C. to 350° C. under a pressure range of from 40 bar to 250 bar. However, both processes have considerable disadvantages:

EP 0 005 203 B1 does not describe the removal of organic hydrocarbons such as benzene or nitrobenzene which are produced in an adiabatic nitration process corresponding to the state of the art. The purification of the waste water according to the teaching of EP 0 005 203 B1 is therefore either insufficient, or the consumption of sodium hydroxide solution in the TPD is very high.

In EP 0 503 387 B1 complete decomposition of nitrobenzene does not succeed, so that a further treatment of the waste water is necessary. The nitrobenzene contained in the waste water moreover is decomposed in the TPD and therefore decreases the yield achieved. The presence of nitric acid in the TPD required according to the teaching of EP 0 503 387 B1 furthermore drives up the process costs in two respects: on the one hand due to the consumption or nitric acid and on the other hand due to the high material stresses as a result of the corrosiveness of the nitric acid and the high investment costs associated with that, for example for a corrosion-resistant tubular reactor lined with titanium. An additional disadvantage winch is not described is also the need for the alkaline waste water initially having to be neutralized (e.g. with additional nitric acid), before this can be converted into an acid pH range by addition of the nitric acid. A relatively large amount of acid is thus necessary.

EP 1 593 654 A1 describes a process for working up alkaline waste waters which are formed during the washing of crude nitrobenzene, wherein the crude nitrobenzene is prepared by adiabatic nitration of benzene with nitrating acid and is then washed in an acid wash and thereafter in an alkaline wash, wherein an alkaline waste water comprising benzene in concentrations of from 100 ppm to 3,000 ppm and nitrobenzene in concentrations of from 1,000 ppm to 10,000 ppm is obtained, wherein benzene and/or nitrobenzene present in undissolved form are then separated out of the alkaline waste water, and the residual benzene and/or nitrobenzene is then optionally removed from the alkaline waste water by stripping, and the alkaline waste water is then heated to temperatures of from 150° C. to 500° C. under increased pressure, with exclusion of oxygen. The waste water treated in such a way can therefore be sent directly to a biological treatment plant without dilution.

EP 0 953 546 B1 describes a process for the degradation of an aromatic nitro compound or of a mixture of two or more of these in waste waters which have a pH of from 7 to 14, in which the waste waters are heated to temperatures of from 150° C. to 350° C. under a pressure of from 10 to 300 bar, wherein at least one aromatic nitro compound carries no hydroxyl group on the aromatic ring. Examples of such aromatic nitro compounds are nitro-hydroxyaromatics, such as mono-, di- and trinitrophenols, mono-, di- and trinitrocresols, mono-, di- and trinitroresorcinols and mono-, di- and trixylenols. Aromatic nitro compounds which carry no hydroxyl group on the aromatic ring are, for example, nitrobenzenes, nitrotoluenes and dinitrotoluenes, EP 0 953 546 B1 states that the waste waters treated in this way can undergo biological purification without problems.

WO 2012/025393 A1 describes the work-up of waste waters which are obtained in the purification of crude aromatic nitro compounds after the nitration of aromatic compounds, and in particular deals with the problems of removal of ammonia, which is formed during the thermal decomposition of nitro compounds. The process described provides the following steps: (a) one-stage or multi-stage washing of the crude aromatic nitro compound to obtain at least one organic phase and at least one aqueous phase, and separating off of the aqueous phase or the aqueous phases, wherein step (a) includes the addition of a base which differs from ammonia, and they (b) optionally removal of organic constituents from at least a part of the aqueous phase or aqueous phases obtained in step (a) by stripping, preferably with steam, subsequently (c) removal of organic compounds from at least a part of the aqueous phase or aqueous phases resulting from step (a) or, respectively, step (b) by thermal and/or oxidative degradation, subsequently (d) depletion of ammonia from at least a part of the aqueous phase or aqueous phases resulting from step (c) by distillation, and subsequently (e) optionally feeding of at least a part of the aqueous phase or aqueous phases resulting from step (d) to a biological waste water treatment. In particular, the ammonia content in the waste water in step (d), which is produced in the nitration of aromatic compounds and subsequent removal of organic constituents, should be reduced. In this connection WO 2012/025393 A1 refers to free ammonia and not dissolved ammonium ions in the waste water after the TPD, which is fed to a biological waste water treatment. From the carbon dioxide present in the alkaline waste water and the ammonia, in fact, ammonium carbonate always also forms to a certain extent, which as a result of its salt character cannot be removed by snipping like ammonia.

There was therefore a need for additional improvements of the process for the work-up of alkaline waste waters which are formed during washing of crude nitrobenzene prepared by adiabatic nitration of benzene. In particular, the process should be simple and economical and comprise a gentle treatment of the entrained organic substances, so that these are not decomposed, but can be recovered from the waste water, before this is sent to a waste water treatment.

SUMMARY

Taking into account this need, the present invention provides a process for the work-up of alkaline waste water which is formed during washing of crude nitrobenzene obtained by—preferably adiabatic—nitration of benzene, wherein (i) the alkaline waste water is heated to a temperature of from 150° C. to 500° C., preferably from 250° C. to 350° C., particularly preferably from 270° C. to 290° C., under an increased pressure with respect to atmospheric pressure, preferably under an absolute pressure of from 50 bar to 350 bar, particularly preferably from 50 bar to 200 bar, very particularly preferably from 70 bar to 130 bar, for preferably a period of from 5 minutes to 120 minutes, particularly preferably from 15 minutes to 30 minutes, with exclusion of oxygen and is then cooled preferably to a temperature of from 60° C. to 100° C. and expanded;

(ii) the waste water obtained in (i) is purified further by stripping with a stripping gas, preferably steam, preferably under an absolute pressure of from 0.1 bar to 5 bar, particularly preferably 0.5 bar to 2 bar and preferably at a temperature of from 40° C. to 160° C., particularly preferably 80° C. to 120° C., and the stripping gas stream loaded with impurities is then cooled to a temperature of from 10° C. to 60° C., preferably from 20° C. to 50° C. particularly preferably from 25° C. to 45° C., very particularly preferably from 30° C. to 40° C.;

(iii) the liquid process product obtained in (ii) by cooling the stripping gas stream loaded with impurities is separated into art aqueous and an organic phase and the organic phase is used further in an aniline production process.

Surprisingly, it has in fact been found that in the process according to the invention the nitrobenzene which enters into step (i) with the alkaline waste water is at least partly reacted there to give aniline, so that the organic phase obtained can advantageously be sent to an aniline production process.

DETAILED DESCRIPTION

Embodiments of the invention are described in more detail in the following. In this context, various embodiments can be combined with one another as desired, if the opposite does not clearly emerge from the context.

In a particularly preferred embodiment, the overall process includes the following steps:

a) nitration of benzene with nitric acid or—preferably—a mixture of nitric acid and sulfuric acid (also called mixed acid in the following) and separating off of the aqueous phase;

b) washing of the organic process product obtained in step a);

c) alkaline washing of the washed organic process product obtained in step b), an alkaline waste water comprising benzene in a concentration of from 100 ppm to 3,000 ppm and nitrobenzene in a concentration of from 1,000 ppm to 10,000 ppm preferably being obtained;

d) optional separation of benzene and/or nitrobenzene from the alkaline waste water obtained in step c);

e) work-up of the alkaline waste water obtained in step c) or step d), including steps (i) to (iii) described above.

The nitration of benzene to give nitrobenzene with nitric acid or a mixture of nitric acid and sulfuric acid (mixed acid) in step a) is carried out in this context by any desired process from the state of the art which is known to the person skilled in the art, as described e.g. in EP 0 436 443 B1, EP 0 771 783 B1, U.S. Pat. No. 6,562,247 B2 or in EP 0 156 199 B1. Since a crude nitrobenzene which comprises excess acid, unleaded benzene, water and organic by-products is obtained in all the processes of the state of the art, the purification according to the invention of the crude nitrobenzene obtained in step a) can in principle be applied to all processes. For example, the nitration can be carried out with dissipation of the heat of reaction (i.e. isothermally or approximately isothermally) or also without dissipation of the heat of reaction in preferably isolated reactors (i.e. adiabatically). However, the reaction of benzene with a mixture of nitric acid and sulfuric acid using an adiabatic process procedure, such as is described in particular in DE 10 2008 048 713 A1, and there in particular in paragraph [0024], is preferred. The crude nitrobenzene prepared in step a) is finally separated from excess acid (if mixed acid is used substantially sulfuric acid) in a separating tank.

The organic phase, which conventionally still comprises traces of acid, obtained in step a) after the phase separation is washed in step b) in one to two, preferably one wash(es) and is then separated from the acid aqueous phase by phase separation (in the case of several washes after each individual wash). In step b) the acid residues which the crude nitrobenzene contains are washed out; this process step is therefore also called an acid wash. Preferably the procedure in this context is such that a pH of <5 (measured at 20° C.) is established in the aqueous phase obtained after the phase separation. Any type of water, e.g., deionized water or steam condensate, can be employed as the wash liquid in step b). The water can also contain dissolved salts. Preferably, aqueous streams obtained in the plant are recycled for carrying out step b).

The organic phase obtained in this way is then washed in step c) in preferably one to two, particularly preferably one alkaline wash(es) with a base, preferably an aqueous solution of a base chosen from the group consisting of sodium hydroxide, sodium carbonate and sodium bicarbonate, and is then separated from the alkaline wash water by phase separation (in the case of several washes after each individual wash). Sodium hydroxide solution is preferably used as the aqueous base solution. The alkaline wash is described in the following by means of sodium hydroxide solution; it is an easy matter for the person skilled in the art to make appropriate modifications if necessary if other bases are used.

Preferably, the sodium hydroxide solution used has a pH of from 9.0 to 14 (measured at 20° C.). The weight ratio of sodium hydroxide solution to organic phase (substantially nitrobenzene) depends on the benzene excess employed in step a) and is preferably between 1:80 and 1:500. The pH of the sodium hydroxide solution used and its weight ratio to the organic phase are established such that acid impurities (e.g. nitrophenols formed as by-products and acid residues which have not been completely removed in step b)), are largely to completely, preferably completely neutralized in step c). Preferably, the base is used in an excess of from 0.5% to 5.0% of theory in step c), particularly preferably from 1.0% to 3.0% of theory and very particularly preferably from 1.5% to 2.5% of theory, in each case based on the nitrophenols contained in the waste water after step b). In this context the decisive value for the nitrophenol content is that determined by gas chromatography.

In the optional step d), undissolved benzene and/or nitrobenzene which are still present in the alkaline waste water from step c) are separated off from this. The benzene and/or nitrobenzene separated off in this way are then preferably sent back to the nitration process, particularly preferably into the crude nitrobenzene. In this context, the separating off of the nitrobenzene present in undissolved form can be carried out by separators, settling tanks or other phase separation apparatuses. A settling tank is preferably used. Preferably, alkaline waste water which comprises benzene in a concentration of from 100 ppm to 1,000 ppm and nitrobenzene in a concentration of from 1,200 ppm to 3,000 ppm is obtained in step d), it is preferable to carry out step d).

In step e) (i) (the TPD) the alkaline waste water, which is obtained from steps c) and d) and is still loaded with organic salts of the nitro-hydroxyaromatics, is heated to a temperature of from 150° C. to 500° C., preferably from 250° C. to 350° C., particularly preferably from 270° C. to 290° C., under an increased pressure with respect to atmospheric pressure, preferably under an absolute pressure of from 50 bar to 350 bar, particularly preferably from 50 bar to 200 bar, very particularly preferably from 70 bar to 130 bar, with exclusion of oxygen. It is also possible for the alkaline waste water to be heated under an inert gas atmosphere or under an inert gas admission pressure of for example, 0.1 bar to 100 bar. Suitable inert gases are e.g. nitrogen and/or argon. Depending on the temperature and where appropriate the inert as admission pressure, the abovementioned pressures are preferably established during heating of the waste waters. The heating of the alkaline waste water and thermal pressure decomposition of the organic constituents such as benzene, nitrobenzene and nitro-hydroxyaromatics is conventionally carried out in this context for 5 minutes to 120 minutes, preferably 15 minutes to 30 minutes. Preferably, the alkaline waste water is then cooled such that it leaves the TPD with a temperature of from 60° C. to 100° C. The cooling is preferably carried out in counter-current flow with the incoming stream with decompression. Steps d) and e) (i) can be carried out according to the state of the art, preferably according to the disclosure of EP 1 593 654 A1.

It is particularly preferable to coordinate the residence time in step e) (i) and the excess of base used in step c) with one another. Thus, in the event of a short residence time in step e) (i), a larger excess of base is advantageous in step c).

In step e) (ii), the waste water obtained in e) (i) is purified further by stripping and the stripping gas stream loaded with impurities is then cooled to a temperature of from 10° C. to 60° C., preferably from 20° C. to 50° C., particularly preferably from 25° C. to 45° C., very particularly preferably from 30° C. to 40° C. Organic constituents still present are removed by this procedure. Preferably, the stripping in the context of the present invention is carried out in counter-current flow in a stripping column, the gas stream of the stripping gas used (preferably steam) and the readily volatile constituents stripped off preferably emerging at the head at the stripping column (vapours) and the stripped waste water preferably being removed at the bottom of the stripping column. The gas stream removed at the head of the stripping column (vapours) is cooled in a condenser to a temperature of from 10° C. to 60° C., preferably from 20° C. to 50° C., particularly preferably from 25° C. to 45° C., very particularly preferably from 30° C. to 40° C. Ammonia stripped off which remains in gaseous form is preferably sent to a technical exhaust air decontamination.

The stripping column is preferably a tubular device with several baffles (e.g. packed beds, structured packings or mass transfer trays) for intensive mass transfer of the gaseous and liquid phase. Appropriate processes and columns are known to the person skilled in the art and are described e.g. in W. Meier, Sulzer, Kolonnen für rektifikation und Absorption, in: Technische Rundschau Sulzer, 2 (1979), page 49 to 61. Preferably, the stripping according to step e) (ii) is carried out under an absolute pressure of from 0.1 bar to 5 bar, particularly preferably 0.5 bar to 2 bar, and preferably at a temperature of from 40° C. to 160° C., particularly preferably 80° C. to 120° C.

In step e) (iii), the liquid stream obtained in step e) (ii) by cooling the gas stream of the stripping gas used (preferably steam) and the readily volatile constituents stripped of are separated into an aqueous and an organic phase. This is carried out in a phase separation apparatus, from which the organics which separate are purged. The stream obtained in this way, which is largely freed from organics (in the preferred embodiment with steam as the stripping gas the so-called vapour water), is preferably sent back partially to completely to the head of the stripping column. The remaining part of the stream which has been largely freed from organics and has not been sent back to the head of the stripping column is preferably sent directly (without further intermediate purification steps) to a waste water treatment, preferably a biological treatment plant.

According to the invention, the organic phase which has been obtained in step (iii) and has been purged out of the phase separation apparatus is sent to an aniline production process. This is preferably a process for the preparation of aniline by catalytic hydrogenation of nitrobenzene. The catalytic hydrogenation of nitrobenzene is preferably carried out in the gas phase with recycling of unreacted hydrogen (circulating as procedure). The feeding of the organic phase from step (iii) can be carried out at various points.

It is thus possible to feed the organic phase from step (iii) to an educt stream of an aniline production plant. For example, in large-scale industrial operation with recycling of unreacted hydrogen, the feed hydrogen, a mixture of freshly fed hydrogen and recycled hydrogen, in any case contains contents of aniline which has not been separated off completely after the reaction has taken place. It is of course also possible to send the organic phase from step (iii) to the product stream of the aniline production plant, preferably after cooling thereof and before the subsequent work-up of the crude aniline by distillation.

EXAMPLES

Content of organic components: gas chromatography (GC), area % are stated.

Content of cations: atomic absorption spectrometry (inductive coupled plasma, ICP), weight contents in ppm are stated.

General Conditions for the Preparation of Nitrobenzene

Nitrobenzene was prepared in an adiabatic process as described in EP 2 168 942 A1. The waste water obtained in the last alkaline wash in this procedure was used in the following examples.

Example 1 (According to the Invention)

The waste water from the alkaline wash was sent to a settling tank in which undissolved benzene and nitrobenzene were separated out. 3.5 tonnes per hour of alkaline waste water which had a content of nitrobenzene of 2,870 ppm, of benzene of 409 ppm and of nitrophenols of 11,809 ppm and a pH of 12.8 (1.8% NaOH excess compared with the starting content of nitrophenols before the alkaline wash) were treated from there with a residence time of 20 min, a temperature of 290° C. and an absolute pressure of 90 bar. The waste water formed was cooled to 80° C. (step (i)). The conversion of nitrobenzene in the TPD is 99%. The waste water was then stripped with direct steam (step (ii)). The stripping column was operated wider an absolute pressure of 1.05 bar. A stream of 3.9 tonnes per hour which substantially comprised water, ammonia and organics was obtained in the sump of the stripping column. The head product of the stripping column was condensed and separated into an aqueous and an organic phase (step (iii)), and 280 kg per hour of the aqueous stream were recycled as reflux into the column. The lower organic phase in the phase separation apparatus was sent into the crude aniline tank of an aniline plant for further processing. The organic phase contained 2.6 kg of aniline, 0.2 kg of nitrobenzene, 1.5 kg of benzene and 1 kg of phenol per hour. The yield of aniline obtained in the TPD, based on nitrobenzene, was 22%.

Example 2 (According to the Invention)

The waste water from the alkaline wash was sent to a settling tank in which undissolved benzene and nitrobenzene were separated out. 3.5 tonnes per hour alkaline waste water which had a content of nitrobenzene of 2,915 ppm, of benzene of 382 ppm and of nitrophenols of 12,051 ppm and a pH of 13.4 (2.3% NaOH excess compared with the initial content of nitrophenols before the alkaline wash) were treated with a residence time of 20 min, 290° C. and an absolute pressure of 90 bar. The waste water formed was cooled to 80° C. (step (i)). The conversion of nitrobenzene in the TPD is 99.9%. The waste water was then stripped with direct steam. The stripping column was operated under an absolute pressure of 1.05 bar. A stream of 3.9 tonnes per hour which substantially comprised water, ammonia and organics was obtained in the sump of the stripping column. The head product of the stripping column was condensed and separated into an aqueous and an organic phase (step (iii)), and 280 kg per hour of the aqueous stream were recycled as reflux into the column. The lower organic phase in the phase separation apparatus is sent to the crude aniline tank of an aniline plant for further processing. The organic phase contains 5.9 kg of aniline, 0.01 kg of nitrobenzene, 1.2 kg of benzene and 0.8 kg of phenol per hour. The yield of aniline obtained in the TPD, based on nitrobenzene, was 49%.

Example 3 (According to the Invention)

The waste water from the alkaline wash was sent into a settling tank in which undissolved benzene and nitrobenzene were separated out. 3.6 tonnes per hour of alkaline waste water which had a content of nitrobenzene of 2,420 ppm, at benzene of 220 ppm and of nitrophenols of 11,234 ppm and a pH of 13.0 (1.8% NaOH excess compared with the initial content of nitrophenols before the alkaline wash) were treated with a residence time of 41 min, 280° C. and an absolute pressure of 106 bar. The waste water formed was then cooled to 80° C. (step (i)). The conversion of nitrobenzene in the TPD is 99.9%. The waste water was then stripped with direct steam. The file stripping column was operated under an absolute pressure of 1.03 bar (step (ii)). A stream of 4.0 tonnes per hour which substantially comprised water, ammonia and organics was obtained in the sump of the stripping column. The head product of the stripping column was condensed and separated into an aqueous and an organic phase (step (iii)), and 680 kg per hour of the aqueous stream were recycled as reflux into the column. The lower organic phase in the phase separation apparatus was sent to the crude aniline tank of an aniline plant for further processing. The organic phase contained 10 kg of aniline, 0.04 kg of nitrobenzene, 0.01 kg of benzene and 0.02 kg of phenol per hour. The yield of aniline obtained in the TPD, based on nitrobenzene, was 99%.

The invention claimed is:

1. A process for working up alkaline waste water which is formed during washing of crude nitrobenzene obtained by nitration of benzene, comprising:
   (i) heating the alkaline waste water to a temperature of from 150° C. to 500° C. under an increased pressure with respect to atmospheric pressure with exclusion of oxygen, wherein the heated alkaline waste water is then cooled and expanded;
   (ii) further purifying the waste water obtained in (i) by stripping with a stripping gas and then cooling the stripping gas stream loaded with impurities is then cooled to a temperature of from 10° C. to 60° C.; and
   (iii) separating the liquid process product obtained in (ii) into an aqueous and an organic phase and further using the organic phase obtained thereby in an aniline production process.

2. The process of claim 1, comprising sending the organic phase obtained in step (iii) to the educt stream of an aniline production plant.

3. The process of claim 1, comprising sending the organic phase obtained in step (iii) to the product stream of an aniline production plant.

4. The process of claim 1, comprising heating of the alkaline waste water in step (i) under an absolute pressure of from 50 bar to 350 bar.

5. The process of claim 1, comprising heating the alkaline waste water in step (i) is carried out for a period of from 5 minutes to 120 minutes.

6. The process of claim 1, comprising, after the heating, cooling the alkaline waste water to a temperature of from 60° C. to 100° C.

7. The process of claim 1, comprising partially recycling the aqueous phase obtained in step (iii) into the stripping of step (ii) and sending the remaining part which is not recycled to a biological treatment plant without further purification steps.

8. The process of claim 1, in which the alkaline waste water used in step (i) originates from step c) or step d) of the following process steps:
   a) nitration of benzene with nitric acid or a mixture of nitric acid and sulfuric acid and separating off of the aqueous phase;
   b) washing of the organic process product obtained in step a);
   c) alkaline washing of the washed organic process product obtained in step b); and
   d) optional separation of benzene and/or nitrobenzene out of the alkaline waste water obtained in step c).

9. The process of claim 8, in which in the alkaline wash in step c) the base is used in an excess of from 0.5% to 5.0% of theory, based on the nitrophenols contained in the waste water after step b).

* * * * *